United States Patent
Kim et al.

(10) Patent No.: US 11,687,074 B2
(45) Date of Patent: Jun. 27, 2023

(54) METHOD FOR CONTROLLING MOVING BODY BASED ON COLLABORATION BETWEEN THE MOVING BODY AND HUMAN, AND APPARATUS FOR CONTROLLING THE MOVING BODY THEREOF

(71) Applicant: KOREA INSTITUTE OF SCIENCE AND TECHNOLOGY, Seoul (KR)

(72) Inventors: Laehyun Kim, Seoul (KR); Da-Hye Kim, Seoul (KR); Seung-jun Oh, Seoul (KR); Eon Jo Hong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 414 days.

(21) Appl. No.: 17/025,187

(22) Filed: Sep. 18, 2020

(65) Prior Publication Data

US 2022/0004184 A1    Jan. 6, 2022

(30) Foreign Application Priority Data

Jul. 6, 2020    (KR) .......................... 10-2020-0082945

(51) Int. Cl.
   *G05D 1/00* (2006.01)
   *G05D 3/00* (2006.01)
   (Continued)

(52) U.S. Cl.
   CPC ........... *G05D 1/0016* (2013.01); *A61B 5/378* (2021.01); *A61B 5/7282* (2013.01); *B60W 40/02* (2013.01);
   (Continued)

(58) Field of Classification Search
   CPC .. G05D 1/0016; G05D 1/0088; G05D 1/0246; A61B 5/378; A61B 5/7282;
   (Continued)

(56) References Cited

U.S. PATENT DOCUMENTS

| | | | |
|---|---|---|---|
| 5,555,495 A * | 9/1996 | Bell ...................... | B60W 40/08 706/905 |
| 2015/0091791 A1* | 4/2015 | Segal .................... | G06F 16/436 345/156 |

(Continued)

FOREIGN PATENT DOCUMENTS

| | | |
|---|---|---|
| JP | 2017509523 A | 4/2017 |
| KR | 1020140077566 A | 6/2014 |
| KR | 101618186 B1 | 5/2016 |

OTHER PUBLICATIONS

Elsevier, Science direct, title: "Bio-signal based control in assistive robots" a survey by Rechy-Ramirez (Year: 2015).*

(Continued)

*Primary Examiner* — Abby Y Lin
*Assistant Examiner* — Sohana Tanju Khayer
(74) *Attorney, Agent, or Firm* — Rabin & Berdo, P.C.

(57) ABSTRACT

The present disclosure relates to technology that controls a remote moving body based on collaboration between the moving body and human, and a method for controlling a moving body includes acquiring a first biosignal indicating an intention to start operation of the moving body from a user, operating the moving body, determining a surrounding situation of the moving body that autonomously controls the driving, providing the user with surrounding information of the moving body for inducing path setting, acquiring a second biosignal evoked by recognition of the surrounding information from the user, setting a driving direction of the moving body, commanding the moving body to automatically perform a driving operation to be carried out in the set driving direction, and acquiring a third biosignal responsive to recognition of a driving error from the user and correcting the driving direction of the moving body to induce driving path resetting.

20 Claims, 13 Drawing Sheets

(51) Int. Cl.
*G06F 7/00* (2006.01)
*G06F 17/00* (2019.01)
*A61B 5/00* (2006.01)
*A61B 5/378* (2021.01)
*G05D 1/02* (2020.01)
*B60W 50/08* (2020.01)
*B60W 40/08* (2012.01)
*B60W 60/00* (2020.01)
*B60W 40/02* (2006.01)
*G06F 3/01* (2006.01)
*G10L 15/22* (2006.01)
*G06V 40/20* (2022.01)
*B60W 50/00* (2006.01)

(52) U.S. Cl.
CPC ............ B60W 40/08 (2013.01); B60W 50/08 (2013.01); B60W 60/001 (2020.02); G05D 1/0088 (2013.01); G05D 1/0246 (2013.01); *B60W 2040/089* (2013.01); *B60W 2040/0872* (2013.01); *B60W 2050/0064* (2013.01); *B60W 2420/42* (2013.01); *G06F 3/015* (2013.01); *G06F 3/017* (2013.01); *G06V 40/20* (2022.01); *G10L 15/22* (2013.01); *G10L 2015/223* (2013.01)

(58) Field of Classification Search
CPC ....... A61B 5/372; B60W 40/02; B60W 40/08; B60W 50/08; B60W 60/001; B60W 2040/0872; B60W 2040/089; B60W 2050/0064; B60W 2420/42; B60W 30/181; B60W 2050/146; B60W 2520/04; B60W 2520/06; B60W 2520/10; G06F 3/015; G06F 3/017; G06V 40/20; G10L 15/22; G10L 2015/223; G06K 9/0053; B60Y 2300/18091
See application file for complete search history.

(56) References Cited

U.S. PATENT DOCUMENTS

| | | | | |
|---|---|---|---|---|
| 2016/0325758 | A1* | 11/2016 | Huang | B62D 1/286 |
| 2017/0091741 | A1* | 3/2017 | Todeschini | A61B 5/369 |
| 2018/0036185 | A1* | 2/2018 | Han | G06F 3/015 |
| 2018/0107275 | A1* | 4/2018 | Chen | G06F 3/015 |
| 2018/0147099 | A1* | 5/2018 | Jones | A61B 5/389 |
| 2019/0077504 | A1* | 3/2019 | Chapman | G01C 21/362 |
| 2019/0101985 | A1* | 4/2019 | Sajda | G06F 3/017 |
| 2020/0205712 | A1* | 7/2020 | Laszlo | A61B 5/377 |
| 2020/0367789 | A1* | 11/2020 | Moffat | A61B 5/398 |
| 2021/0124422 | A1* | 4/2021 | Forsland | G10L 15/22 |
| 2021/0380139 | A1* | 12/2021 | Taveira | B60W 60/0025 |
| 2022/0164029 | A1* | 5/2022 | Chin | G06F 3/015 |

OTHER PUBLICATIONS

Hindawi publishing corporation Bio med research international title: "Brain computer interface for control of wheelchair using fuzzy neural networks" by Abiyev (Year: 2016).*

* cited by examiner

METHOD FOR CONTROLLING MOVING BODY BASED ON COLLABORATION BETWEEN THE MOVING BODY AND HUMAN, AND APPARATUS FOR CONTROLLING THE MOVING BODY THEREOF

CROSS-REFERENCE TO RELATED APPLICATIONS

This application claims priority under 35 U.S.C. § 119 to Korean Patent Application No. 10-2020-0082945 filed on Jul. 6, 2020 in the Korean Intellectual Property Office, the disclosure of which is incorporated herein by reference in its entirety.

TECHNICAL FIELD

The present disclosure relates to technology that controls a remote moving body using human biosignals, and more particularly, to a method for controlling a moving body based on collaboration between the moving body and human using brain-computer interface (BCI), and a recording medium having the method recorded thereon and an apparatus for controlling a moving body according to the method.

BACKGROUND

Brain-computer interface (BCI) technology refers to technology that directly controls a computer or an external device by directly connecting the brain in a living being to the computer or the external device and analyzing the activity of the brain or electroencephalogram (EEG) without existing input/output devices such as audio, video and motion input/output devices. Accordingly, using the BCI technology, decision making resulting from the brain's information processing is transmitted to a system sensor using specific brain waves when a user thinks and determines without using languages or physical behaviors to enable the computer to execute the corresponding command. A method of manipulating the computer using EEG, not a keyboard or a mouse, is useful for people with disabled or impaired physical activities, and can be applied to communication, movement and activity assistance for patients or disabled people, and accordingly research on BCI has been continuously conducted. The related literature introduced below describes interface technology for communication with computers based on EEG.

Recently, the number of disabled people living alone increases and patients with serious illness stay at home and have limited access to normal social activities, and accordingly there is an increasing need for remote moving bodies to help them to do outdoor social activities. With the increasing interest and demand for so-called 'activity assistant moving bodies', there is a growing trend in markets and related technology suggestions each year. Accordingly, when BCI technology is combined with activity assistant moving bodies, it is expected that many care and activity assistant services (class, participation in meeting, trip, exploration, etc.) that have been provided through labor will be provided by users' own intention.

However, most of activity assistant moving bodies including remote moving bodies are controlled using joysticks or touch as input means, and voice recognition control was recently introduced. These traditional methods have control limitations because they are difficult for users with impaired physical activities to manipulate and impossible to provide feedback to incorrect selection. Accordingly, BCI technology that controls remote moving bodies by thoughts alone may be an answer to disabled people or patients having difficult in doing outdoor activities. However, the performance of BCI is lower than other media in terms of external device control accuracy, and thus technology for improving the BCI performance is necessary for commercialization.

The development of image recognition of space or autonomous driving technology introduces a smart remote moving body that can control the driving itself. The corresponding technical field includes technical means that recognizes a space in which the moving body is located using a depth camera, a stereo camera or different types of sensors, and performs autonomous path navigation and driving.

The activity assistant moving body and the smart remote moving body introduced previously are designed from two opposite points of view of remote control and autonomous driving, respectively, and experiments reveal that they cannot achieve effective control in specific situations and environments. Accordingly, there is a need for development of BCI-based smart control technology for the remote moving body to overcome the limitation in controlling activity assistant moving bodies that help human activities such as remote moving bodies, and help the elderly and disabled having difficulties in doing physical activities to engage in social activities themselves, and an approach to optimize the command execution according to the technology.

RELATED LITERATURES

[Patent Literature]
Korean Patent Publication No. 2014-0077566 "Method and apparatus for controlling a moving object using brain waves and recording medium having recorded thereon a program for performing the method"

SUMMARY

Since a large amount of labor is still required to control a moving body that helps human social activities at a remote area or it is inconvenient for a user to input a command for the moving body, the present disclosure is designed to solve these problems. Further, in the control of the moving body on the spot, simple remote control for the moving body or a single technical means of autonomous driving technology is inefficient, so the present disclosure is designed to solve this drawback. Additionally, in the control of the remote moving body based on electroencephalogram (EEG), since the performance degrades due to the presence of a large amount of noise in the measured EEG signal or difficulty in interpreting the acquired EEG, the present disclosure is designed to overcome this limitation.

To solve the above-described technical problem, a method for controlling a moving body according to an embodiment of the present disclosure includes (a) acquiring, by an apparatus for controlling a moving body, a first biosignal indicating an intention to start operation of the moving body from a user, and operating the moving body, (b) determining, by the apparatus for controlling a moving body, a surrounding situation of the moving body that autonomously controls the driving, providing the user with surrounding information of the moving body for inducing path setting, acquiring a second biosignal evoked by recognition of the surrounding information from the user, and setting a driving direction of the moving body, (c) commanding, by the apparatus for controlling a moving body, the moving body to automatically perform a driving operation to be carried out in the set driving direction, and (d) acquiring, by the apparatus for controlling a moving body, a third biosignal responsive to recognition of a driving error from the user and correcting the driving direction of the moving body to induce driving path resetting.

In the method for controlling a moving body according to an embodiment, the first biosignal, the second biosignal and the third biosignal may be different types of EEG signals acquired through one EEG measuring means.

In the method for controlling a moving body according to an embodiment, the step (a) may include (a1) receiving inputs of biosignals from the user having recognized the moving body, and acquiring the first biosignal indicating the intention to start the operation of the moving body among the inputted biosignals, and (a2) operating the moving body in response to the first biosignal and waiting for the user's driving direction selection.

In the method for controlling a moving body according to an embodiment, the step (b) may include (b1) when it is determined that collaboration between the moving body and the user is necessary to control the driving of the moving body based on the surrounding situation, providing the user with the surrounding information including at least one of a surrounding map, a surrounding image or a driving path of the moving body in a form of visual stimulation, (b2) acquiring the second biosignal evoked by recognition of the surrounding information from the user, and identifying one of a plurality of candidate paths included in the surrounding information, and (b3) determining a detailed driving direction of the moving body based on the identified candidate path.

In the method for controlling a moving body according to an embodiment, the step (b1) may include visualizing and displaying the surrounding information to allow the user to visually distinguish the plurality of candidate paths on which the moving body may drive, when the surrounding situation collected by the moving body satisfies a preset control change condition from the moving body to the user. Additionally, the step (b2) may include acquiring the second biosignal from the user having recognized the visual stimulation of the surrounding information, and identifying the user's intended candidate path. Additionally, the step (b3) may include extracting a spontaneous biosignal elicited by motor imagery (MI) from the second biosignal, and determining the detailed driving direction of the moving body intended by the user based on the identified candidate path.

In the method for controlling a moving body according to an embodiment, the step (b) may include (b4) receiving the surrounding information including at least one of a surrounding map, a surrounding image or a driving path of the moving body, and identifying a junction near a current driving path of the moving body, (b5) providing the user with type information associated with a driving path at a first estimated time at which the moving body approaches the identified junction in a form of visual stimulation, and (b6) acquiring the second biosignal from the user having recognized the visual stimulation at a second estimated time at which the moving body approaches the identified junction, and determining the driving direction of the moving body. Additionally, the first estimated time and the second estimated time may be adjusted, taking a remaining distance to the junction and a speed of the moving body into account.

In the method for controlling a moving body according to an embodiment, the step (d) may include (d1) acquiring the third biosignal responsive to recognition of a driving error from the user, and investigating if the set driving direction mismatches the user's intention, (d2) as a result of the investigation, when there is an error in the set driving direction, commanding the moving body to rotate at a same position to correct the driving direction, and (d3) when a biosignal indicating an intention to start operation is acquired in the user's desired driving direction while the moving body is rotating, commanding the moving body to perform an actual driving operation along the driving path reset to the corresponding direction.

In the method for controlling a moving body according to an embodiment, the first biosignal may be at least one of an EEG double blink signal acquired through an EEG measuring means, an audio signal acquired through a microphone or a motion or gesture signal acquired through a camera, the second biosignal may be a steady-state visual evoked potential (SSVEP) signal or an MI signal acquired through the EEG measuring means, and include an EEG signal evoked by the user's visual recognition of the plurality of candidate paths included in the surrounding information or MI, and the third biosignal may be an error-related potential (ErrP) signal acquired through the EEG measuring means.

In the method for controlling a moving body according to an embodiment, preferably, the step (a) does not move to the step (b), the step (c) and the step (d) and is on standby until the first biosignal is acquired among the plurality of types of biosignals inputted from the user, the step (b) does not move to the step (c) and is on standby until the second biosignal is acquired among the plurality of types of biosignals inputted from the user, and after the step (c) is completed, the step (a) or the step (b) is performed to repeat the setting of the driving direction and the operation.

The method for controlling a moving body according to an embodiment may further include (e) acquiring, by the apparatus for controlling a moving body, a fourth biosignal responsive to recognition of an emergency situation from the user, and commanding the moving body to stop.

Meanwhile, hereinafter, there is provided a computer-readable recording medium having recorded thereon a program for enabling a computer to perform the above-described method for controlling a moving body.

To solve the above-described technical problem, an apparatus for controlling a moving body based on brain-computer interface (BCI) according to another embodiment of the present disclosure includes an input unit to receives inputs of a plurality of types of biosignals measured from a user, a processing unit to generate a control signal for controlling the moving body according to the type of the biosignal, and a visual stimulation generation means to visualize and display surrounding information to allow the user to visually distinguish a plurality of candidate paths on which the moving body may drive, wherein the processing unit acquires a first biosignal indicating an intention to start operation of the moving body from the user, operates the moving body, determines surrounding situation of the moving body that autonomously controls the driving, when the surrounding situation collected by the moving body satisfies a preset control change condition from the moving body to the user, provides the user with surrounding information of the moving body for inducing path setting through the visual stimulation generation means, acquires a second biosignal evoked by recognition of the surrounding information from the user, sets a driving direction of the moving body, commands the moving body to automatically perform a driving operation to be carried out in the set driving direction, acquires a third biosignal responsive to recognition of a driving error from the user, and corrects the driving direction of the moving body to induce driving path resetting.

In the apparatus for controlling a moving body according to another embodiment, when it is determined that collaboration between the moving body and the user is necessary to control the driving of the moving body based on the surrounding situation, the processing unit may provide the user with the surrounding information including at least one of a surrounding map, a surrounding image or a driving path of the moving body in a form of visual stimulation, acquire the second biosignal evoked by recognition of the surrounding information from the user, identify one of the plurality of candidate paths included in the surrounding information, and determine a detailed driving direction of the moving body based on the identified candidate path.

Additionally, in the apparatus for controlling a moving body according to another embodiment, the processing unit may acquire the second biosignal from the user having recognized the visual stimulation of the surrounding information, identify the user's intended candidate path, extract a spontaneous biosignal elicited by MI from the second biosignal, and determine the detailed driving direction of the moving body intended by the user based on the identified candidate path.

In the apparatus for controlling a moving body according to another embodiment, the processing unit may receive the surrounding information including at least one of a surrounding map, a surrounding image or a driving path of the moving body, identify a junction near a current driving path of the moving body, provide the user with type information associated with a driving path at a first estimated time at which the moving body approaches the identified junction in a form of visual stimulation, acquire the second biosignal from the user having recognized the visual stimulation at a second estimated time at which the moving body approaches the identified junction, and determine the driving direction of the moving body, and the first estimated time and the second estimated time may be adjusted, taking a remaining distance to the junction and a speed of the moving body into account.

In the apparatus for controlling a moving body according to another embodiment, the processing unit may acquire the third biosignal responsive to recognition of a driving error from the user, investigate if the set driving direction mismatches the user's intention, as a result of the investigation, when there is an error in the set driving direction, command the moving body to rotate at a same position to correct the driving direction, and when a biosignal indicating an intention to start operation is acquired in the user's desired driving direction while the moving body is rotating, command the moving body to perform an actual driving operation along the driving path reset to the corresponding direction.

In the apparatus for controlling a moving body according to another embodiment, the first biosignal may be at least one of an EEG double blink signal acquired through an EEG measuring means, an audio signal acquired through a microphone or a motion or gesture signal acquired through a camera, the second biosignal may be an SSVEP signal or an MI signal acquired through the EEG measuring means, and include an EEG signal evoked by the user's visual recognition of the plurality of candidate paths included in the surrounding information or MI, and the third biosignal may be an ErrP signal acquired through the EEG measuring means.

The embodiments of the present disclosure identify each of various EEGs of a user, such as an EEG indicating the operation of a BCI system through collaboration between the moving body and the user, an EEG evoked by visual stimulation, an EEG evoked by MI and an EEG evoked by error response, and efficiently control the smart moving body based on information associated with a driving path provided by the moving body, thereby improving the processing rate which is the disadvantage of BCI, and accurately set a detailed driving path of the user's desired target object by sequential BCI control and control the moving body to drive according to the user's desired destination, thereby inducing the user with physical impairment to do active and independent activities according to the user's intention and enhancing the self-esteem as well as reducing the labor, time and cost required to help the user.

DETAILED DESCRIPTION OF EMBODIMENTS

Prior to describing the embodiments of the present disclosure, after a brief introduction of the practical problem of the conventional technical means in an environment in which the embodiments of the present disclosure are implemented, the technical principle adopted by the embodiments of the present disclosure designed to solve the problem will be presented.

Figure 1:
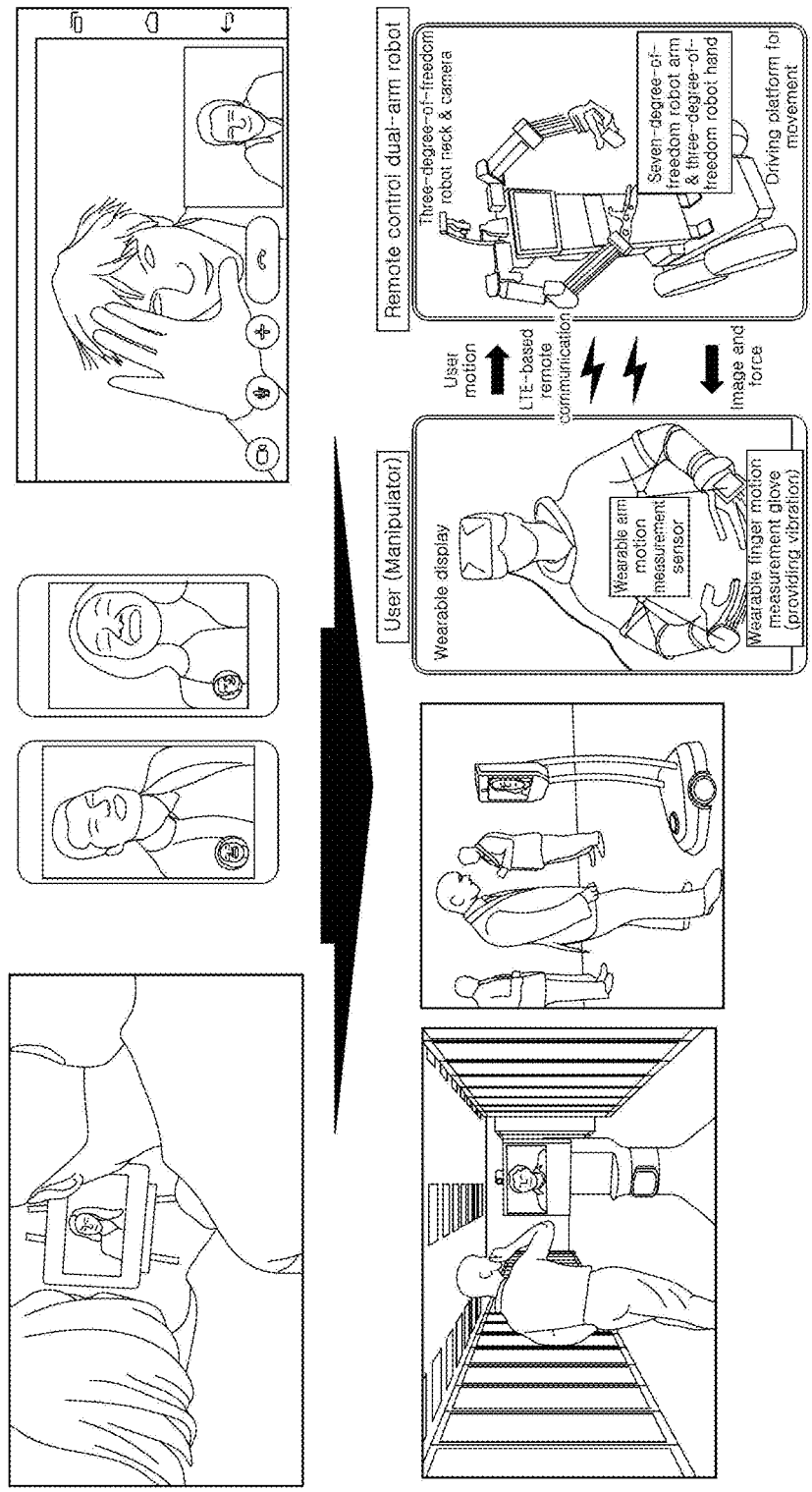
FIG. 1 is a diagram for introducing problems inherent in the technical field in which the present disclosure may be used.

FIG. 1 is a diagram for introducing problems inherent in the technical field in which the present disclosure may be used.

Referring to FIG. 1, remote tasks for communication with persons located in remote places, for example, video conferencing and remote teaching and learning are performed when the persons located in the remote places establish connections, so it is difficult to achieve user-driven video conferencing. As populations are aging and the number of disabled people living alone increases, there is a growing issue related to social activities of the elderly and disabled, and accordingly, the need for social activity assistant moving bodies is increasing. Currently, a variety of remote moving bodies are developed for people with disabilities or seniors with impaired physical mobility and ordinary people who want to perform remote tasks. Particularly, studies on remote moving bodies are aimed at assisting user-driven social activities (participation in meeting, class, trip, exploration, etc.) at remote areas, and achieving performance improvement for practical brain-computer interface (BCI)-based robot control.

However, input methods for remote moving bodies currently available on the market adopt methods using voice commands instructing the driving directions of the moving bodies by manipulating joysticks using the mouth or facial muscles or repeatedly pressing buttons, or methods of driving toward the set destinations while avoiding obstacles. These traditional methods require much time and efforts for users with difficulty doing physical activities to get accustomed to the input methods, and have restrictions on freedom because the users have to set the target positions within only preset ranges and drive according to the set target positions.

Accordingly, the embodiments of the present disclosure as described below propose a technical means that acquires users' biosignals, understands the users' intention more conveniently and actively, and transmits their commands to remote moving bodies and technology that allows the users to freely control the driving at remote areas. To this end, the embodiments of the present disclosure adopt BCI.

Approaches to BCI largely include a simultaneous multichannel extracellular single cell recording technique and a noninvasive method using electroencephalogram (EEG). The former, electrode based BCI, is a highly invasive method including inserting recording electrodes into the cerebral cortex, and has an advantage that it is possible to accurately measure the activities of neurons, but its disadvantage is the insertion of the recording electrodes into the cerebral cortex. In contrast, the latter, EEG based BCI, is not easy to interpret measured EEG signals due to much noise. Considering universality and convenience of signal acquisition, the embodiments of the present disclosure adopt the latter, EEG based BCI.

Hereinafter, the embodiments of the present disclosure will be described in detail with reference to the accompanying drawings. However, in the following description and the accompanying drawings, a detailed description of known function or element that may render the key subject matter of the present disclosure ambiguous is omitted herein. In addition, the term 'comprises' when used in this specification, does not preclude the presence or addition of one or more other elements, unless the context clearly indicates otherwise.

Additionally, the terms "first", "second", and the like may be used to describe various elements, but the elements should not be limited by the terms. These terms may be used to distinguish one element from another. For example, a first element may be called a second element without departing from the scope of protection of the present disclosure, and likewise, a second element may be called a first element.

The terminology used herein is for the purpose of describing particular embodiments only and is not intended to be limiting of the present disclosure. As used herein, the singular forms are intended to include the plural forms as well, unless the context clearly indicates otherwise. It will be understood that the term "comprises" or "includes" when used in this specification, specifies the presence of stated features, integers, steps, operations, elements, components or groups thereof, but does not preclude the presence or addition of one or more other features, integers, steps, operations, elements, components, or groups thereof.

Unless otherwise defined, all terms including technical and scientific terms as used herein have the same meaning as commonly understood by those having ordinary skill in the technical field pertaining to the present disclosure. It will be further understood that terms, such as those defined in commonly used dictionaries, should be interpreted as having a meaning that is consistent with their meaning in the context of the relevant art, and will not be interpreted in an idealized or overly formal sense unless expressly so defined herein.

Figure 2:
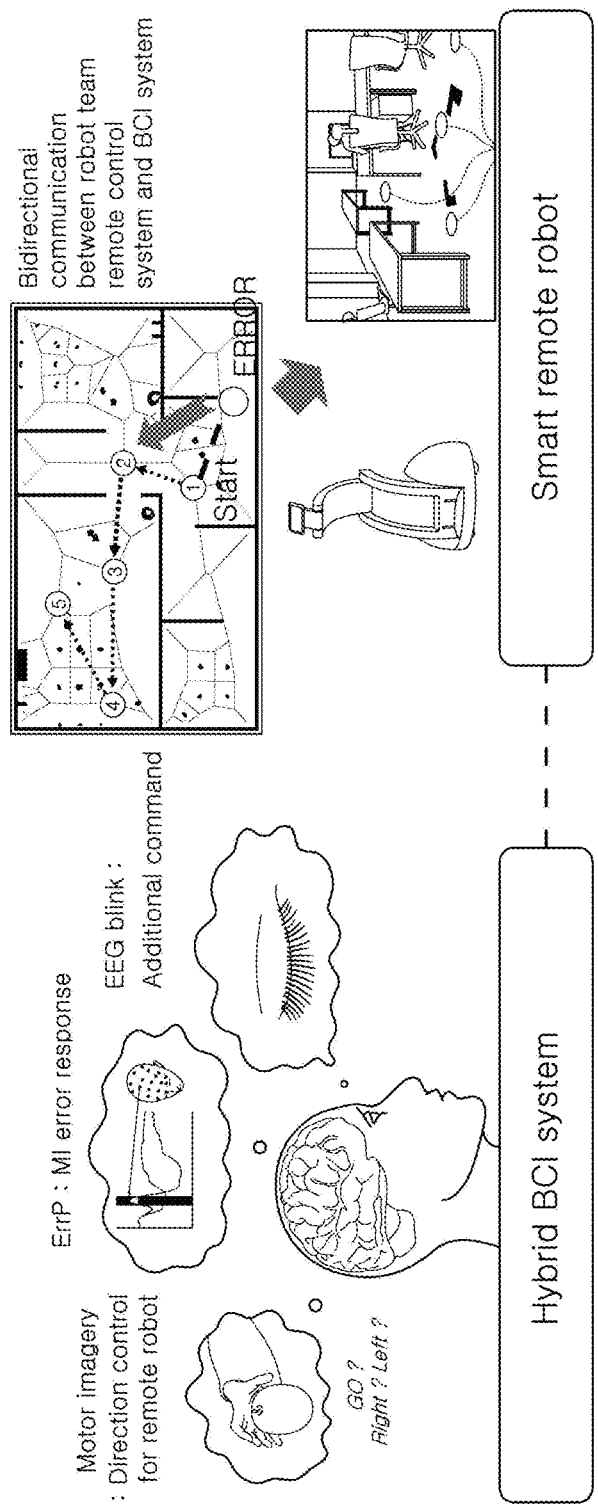
FIG. 2 is a conceptual diagram illustrating a relationship in the system operation through analysis of various electroencephalogram (EEG) patterns based on measured EEG according to an embodiment of the present disclosure.

FIG. 2 is a conceptual diagram illustrating a relationship in the operation of a remote moving body through analysis of various EEG patterns based on measured EEG according to an embodiment of the present disclosure.

As shown in FIG. 2, the BCI-based remote moving body control system analyzes various EEG patterns to control the remote moving body based on biosignals, and through this, controls the remote moving body. For example, in the EEG patterns, an EEG blink signal from the frontal lobe is acquired and used as a system activation trigger signal and a system termination signal according to the type, and a driving path of the remote moving body is selected and set through the EEG pattern of motor imagery (MI) or steady-state visual evoked potential (SSVEP). Additionally, to correct an error in the driving direction, an incorrect driving direction is reset using a biosignal associated with error recognition.

Particularly, the embodiments of the present disclosure do not completely rely on autonomous driving technology only by the remote moving body (a smart remote robot) or the user's remote control/adjustment, and rather, collect information associated with a surrounding situation while the moving body controls the driving itself, and when a specific condition is satisfied, perform collaborative bidirectional communication to induce the control change from the moving body to the user. That is, when it is determined that collaboration between the moving body and the user is necessary to cope with the current surrounding situation, surrounding information is provided to the user to induce the user to intervene in the driving control of the moving body. To this end, the following technical elements are introduced.

1) The remote moving body that controls the driving itself determines a surrounding situation and transmits surrounding information to the user according to whether collaboration with the user is necessary 2) Optimization of commands for controlling the moving body using BCI 3) Hybrid control of autonomous driving of the remote moving body and the user's control command in the driving control of the moving body Hereinafter, the embodiments of the present disclosure designed through the above-described technical elements will be described in detail.

Figure 3:
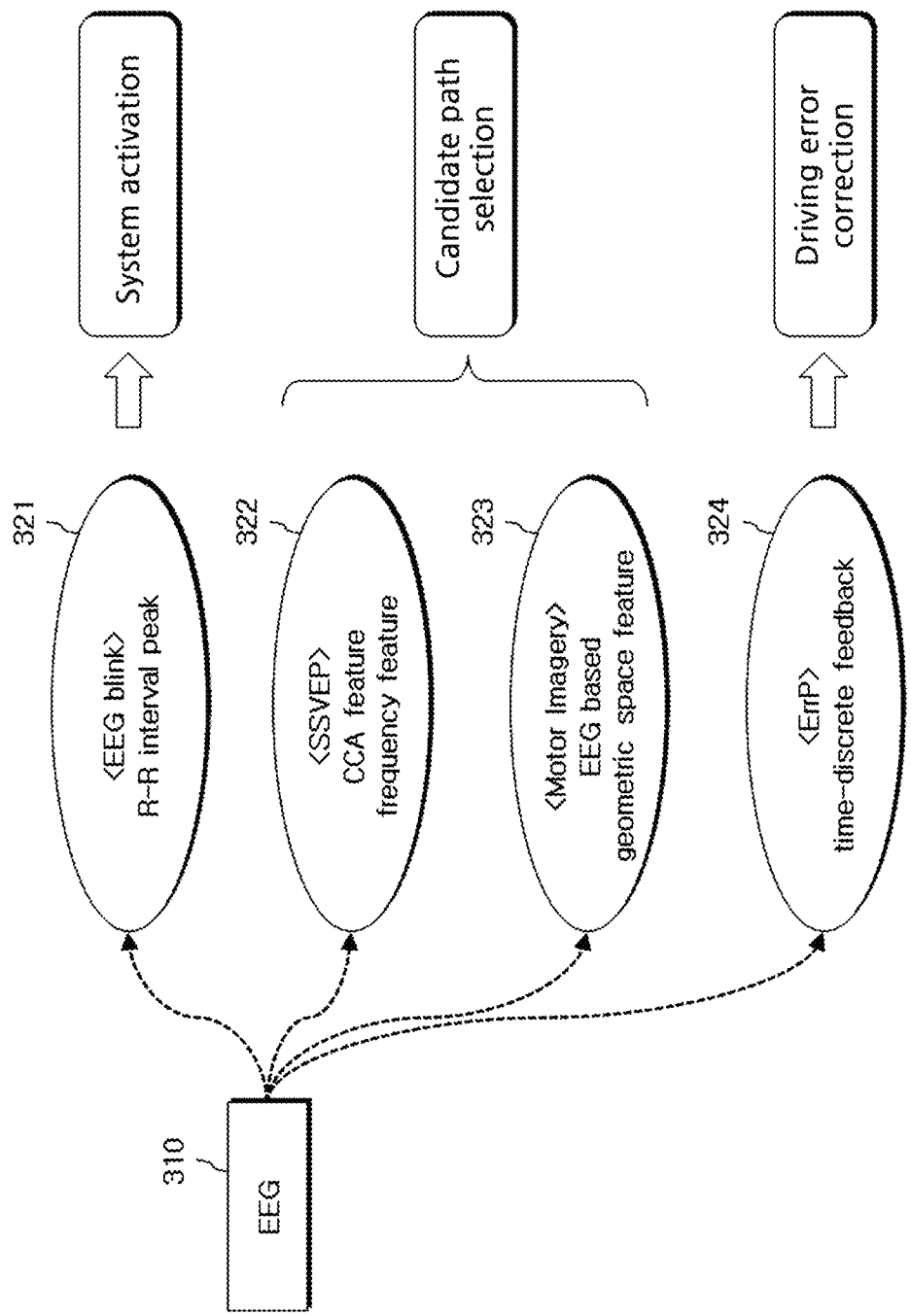
FIG. 3 is a diagram illustrating the type of EEG signal used in a method for controlling a moving body according to embodiments of the present disclosure.

FIG. 3 is a diagram illustrating the type of EEG signal used in a method for controlling a moving body according to embodiments of the present disclosure.

Although there are various available means for interaction between human and robot, the embodiments of the present disclosure intend to carry out interaction by use of only a minimum of communication means as possible. This single communication means is essentially for maximizing user convenience. Accordingly, various biosignals used in the embodiments of the present disclosure are preferably different types EEG signals acquired through one EEG measuring means. That is, the remote moving body is controlled through analysis of various EEG patterns with an aim to control the driving based on unimodal EEG.

Referring to FIG. 3, first, an electroencephalogram (EEG) 310 is inputted from the user through an EEG sensor. The EEG includes a set of various types of EEG signals, and the embodiments of the present disclosure pay attention to the following four types of EEGs.

The first type of EEG signal is an "EEG blink" signal 321. The EEG blink is an EEG evoked by "intentional eye blink", and in the field of general EEG processing technology, it may be regarded as noise and removed in some instances, but in the embodiments of the present disclosure, it acts as an on/off switch to activate the operation of the moving body control system. That is, the EEG blink signal from the frontal lobe in the EEG pattern is acquired and used as an activation trigger signal of the system, thereby controlling the activation of the system at a desired time. Particularly, as opposed to an electrooculogram (EOG) signal based on electromyogram, the EEG blink signal can be acquired through a single EEG measurement sensor without an additional sensor, thereby maintaining unimodality.

The second type of EEG signal is a "steady-state visual evoked potential (SSVEP)" signal 322. The SSVEP is an electrical signal that can be measured at the parietal and occipital lobes in which the visual cortex is positioned in response to visual stimulation, and the embodiments of the present disclosure may identify each candidate path through different visual representations corresponding to a plurality of candidate paths. For example, a driving direction icon or arrow indicating each candidate path for a plurality of driving paths confronted at a junction may be presented to the user as a visual stimulation pattern to induce the user to recognize stimulation. It is possible to select a desired direction or path from the plurality of driving directions or paths with high accuracy through the SSVEP pattern.

The third type of EEG signal is a "motor imagery (MI)" signal 323. In the same way as the SSVEP signal, the embodiments of the present disclosure use the MI signal as a means for acquiring an MI pattern for the driving direction of the moving body from the user and selecting a desired direction or path from a plurality of driving directions or paths. That is, it is possible to select a driving path by using at least one of the SSVEP signal 322 or the MI signal 323 to control the direction of the moving body.

The fourth type of EEG signal is an "error-related potential (ErrP)" signal 324. The ErrP is an EEG pattern of a human observer generated when a target object, for example, the moving body makes a mistake, and helps to correct the mistake of the moving body through the ErrP signal pattern related to error recognition. That is, the ErrP signal evoked by the user's recognition of an error in the driving of the moving body is detected to induce the correction of the driving error quickly.

Figure 4:
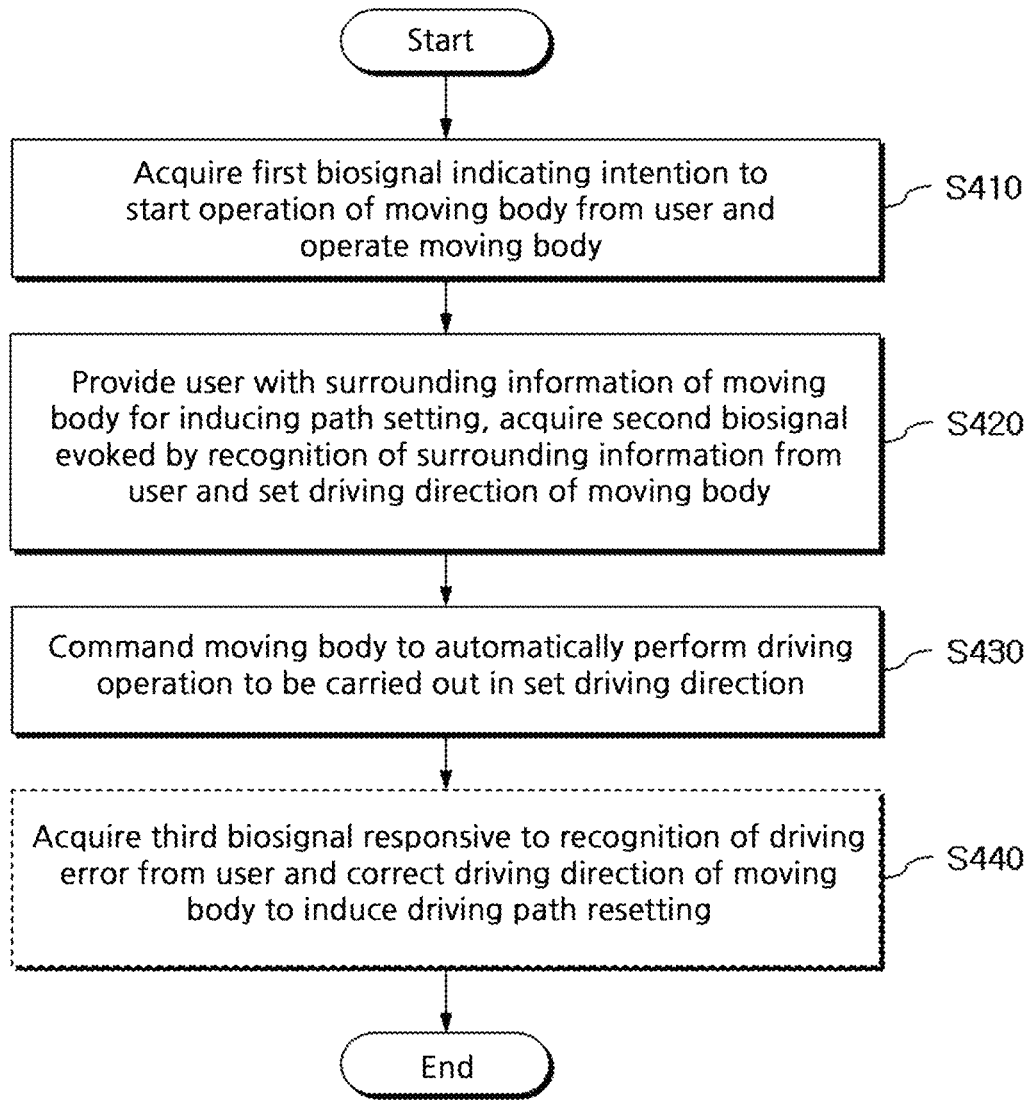
FIG. 4 is a flowchart showing a method for controlling a moving body based on brain-computer interface (BCI) according to an embodiment of the present disclosure.

FIG. 4 is a flowchart showing a method for controlling a moving body based on BCI according to an embodiment of the present disclosure, and on the premise that there is a means for acquiring biosignals from the user, presents a series of processes of generating a control signal for controlling a robot by translation of the biosignal inputted from the user.

In S410, the apparatus for controlling a moving body acquires a first biosignal indicating an intention to start the operation of the moving body from the user and operates the moving body.

Biosignals acquired from human come in different types, and it is very difficult to identify each biosignal or understand its meaning, so the moving body control process as described below follows the procedure according to the time-series determination process. The process does not move to the next step and is on standby until the first biosignal indicating an intention to start the operation of the moving body is acquired among the plurality of types of biosignals inputted from the user. When the first biosignal defined as indicating an intention to start the operation of the moving body is detected among various biosignals, the moving body is operated and an input of a biosignal to monitor next is detected. In this instance, the first biosignal may be used as a trigger signal for the user to operate the remote moving body through an EEG double blink signal among various EEG patterns. Here, the first biosignal may include at least one of an EEG double blink signal acquired through an EEG measuring means, an audio signal acquired through a microphone, or a motion or gesture signal acquired through a camera.

In S420, the apparatus for controlling a moving body determines a surrounding situation of the moving body that controls the driving itself, provides the user with surrounding information of the moving body for inducing the path setting, acquires a second biosignal evoked by recognition of the surrounding information from the user, and sets a driving direction of the moving body. That is, after the moving body determines the situation itself, when it is determined that collaboration between the moving body and the user is necessary, necessary information is transmitted to the user. In this instance, for the determination, it is desirable to preset a control change condition from the moving body to the user. In the embodiments of the present disclosure, the user does not unilaterally give a control command to the moving body, and rather, a more effective control method through collaboration between the moving body and the user is adopted, and the situation requiring collaboration is determined based on whether the control change condition is satisfied or not. Additionally, BCI using EEG is adopted for communication between a machine such as the moving body and a human such as the user. The control change condition may be set based on experience on the spot, taking into account an environment and condition in which the moving body is used, and an example of the collaborative control method will be described in more detail through FIG. 8 below.

For the surrounding information of the moving body at the remote area, the apparatus for controlling a moving body may provide the user with a surrounding map and information associated with the type of road ahead (for example, a three-way junction), acquire a second biosignal evoked by visual stimulation for road selection from the user and identify an object selected by the user. In this process, when the user selects any one of driving directions in a situation in which the type of road on which the remote moving body will drive is presented, a technique for accurately recognizing the user's selection is provided.

To this end, the embodiments of the present disclosure may make use of a spontaneous biosignal elicited by MI among various biosignals that can be acquired from human. Particularly, visual stimulation provided to the user is preferably given to distinguish a plurality of driving paths or directions. First, direction information according to the type of road ahead is visualized and displayed as an arrow or an icon on the visual display for the remote area to acquire a spontaneous biosignal related to a direction in which the user wants to travel. Then, the apparatus for controlling a moving body may acquire a spontaneous biosignal evoked by visual information, and extract signal features included in the acquired biosignal to identify the user's intended driving direction. Here, the second biosignal is an SSVEP signal or an MI signal acquired through the EEG measuring means, and may include an EEG signal pattern evoked by the user's visual recognition of the plurality of candidate paths included in the surrounding information or MI. When the first biosignal indicating an intention to start the operation of the system is acquired, different driving direction information displays corresponding to each of the plurality of candidate paths may be activated and provided to the user.

It is also desirable that this process does not move to the next step and is on standby until the second biosignal related to the remote area surrounding information is acquired among the plurality of types of biosignals inputted from the user. This is because it is necessary to identify the candidate path/direction selected by the user before the moving body performs a specific operation. The user may set the driving direction (for example, three types of directions including Right/Left/Go) of the moving body as the second biosignal according to the type of road provided from the apparatus for controlling a moving body.

In S430, the apparatus for controlling a moving body commands the moving body to automatically perform a driving operation to be carried out in the driving direction set through S420. That is, the moving body is allowed to automatically start a driving operation in the previously set direction through the MI signal pattern. When the set direction is Turn Right or Turn Left, not Go Straight, the remote moving body may perform the driving operation along the corresponding direction. In this instance, so long as a third biosignal (responsive to recognition of a driving error) described below is not generated for a preset period (for example, a short time of 3 seconds or less), the moving body is configured to automatically drive in the previously set driving direction, thereby achieving faster operation.

After this step is completed, the process may return to S410 or S420 to repeat the driving direction setting and the operation. Selection at a branch confronted on the driving path may be determined through repetition of this process.

Subsequently, in S440, a third biosignal responsive to recognition of a driving error may be acquired from the user, and the driving direction of the moving body may be corrected to induce the resetting of the driving path. This process may optionally include processing an error in driving direction (or an emergency situation), and its detailed description will be provided through FIG. 9 below. When a biosignal responsive to recognition of an incorrectly set driving direction (a driving error) is acquired from the user, the apparatus for controlling a moving body induces the remote moving body to correct the driving direction. To this end, from the perspective of implementation, the apparatus for controlling a moving body monitors if a biosignal indicating recognition of an error in the identified driving direction is inputted.

In the above-described moving body control process, the first biosignal, the second biosignal and the third biosignal are preferably different types of EEG signals acquired through one EEG measuring means. That is, it is possible to effectively control the remote moving body by analyzing various EEG patterns based on unimodal EEG.

Figure 5:
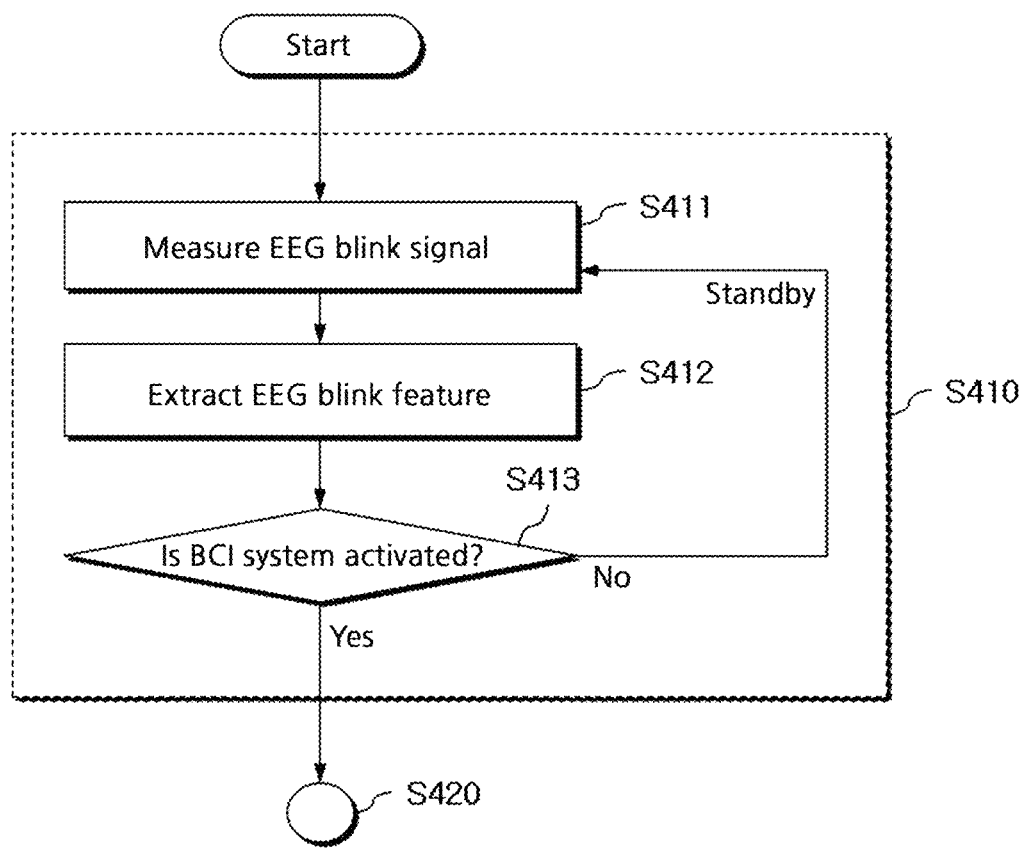
FIG. 5 is a detailed flowchart showing a process of activating a BCI system in the method for controlling a moving body of FIG. 4 according to an embodiment of the present disclosure.

FIG. 5 is a detailed flowchart showing the process (S410) of activating the BCI system in the method for controlling a moving body of FIG. 4 according to an embodiment of the present disclosure.

In S411, the apparatus for controlling a moving body receives inputs of biosignals (for example, an EEG blink signal) from the user having recognized the moving body or the system, and in S412, the apparatus acquires a first biosignal indicating an intention to start the operation of the moving body or the system among the previously inputted biosignals. Subsequently, in S413, the apparatus determines if the system using BCI is activated, and when the system is activated, operates the moving body or the system in response to the first biosignal, and performs S420 to wait for the user's driving direction selection. On the contrary, when the system is not activated, the apparatus returns to S411 and waits for EEG blink signal measurement.

In summary, the apparatus receives inputs of biosignals from the user having recognized the moving body, and acquires a first biosignal indicating an intention to start the operation of the moving body among the inputted biosignals. Subsequently, the apparatus operates the moving body in response to the first biosignal and waits for the user's driving direction selection.

Figure 6:
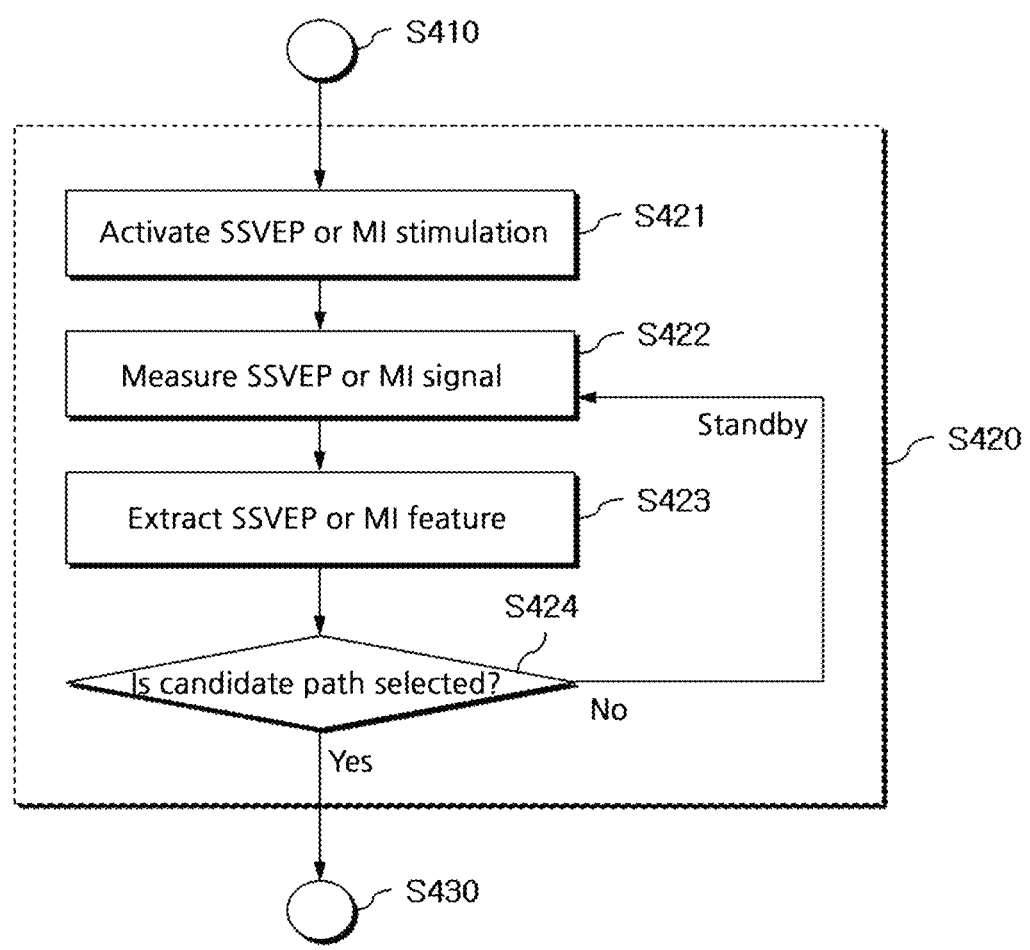
FIG. 6 is a detailed flowchart showing a process of selecting a candidate path in the method for controlling a moving body of FIG. 4 according to an embodiment of the present disclosure.

FIG. 6 is a detailed flowchart showing the process (S420) of selecting a candidate path in the method for controlling a moving body of FIG. 4 according to an embodiment of the present disclosure.

In S421, the apparatus for controlling a moving body differently sets visual stimulation as an arrow, an icon or a symbol for each of a plurality of candidate paths, and provides the user with the visual stimulation (for example, SSVEP stimulation or MI stimulation) corresponding to the plurality of candidate paths. Subsequently, in S422, the apparatus receives inputs of biosignals from the user having recognized the visual stimulation corresponding to any one of the plurality of candidate paths, and in S423, extracts signal features from a second biosignal evoked by the visual stimulation (for example, an SSVEP signal or an MI signal) among the previously inputted biosignals. Subsequently, in S424, the apparatus identifies an object selected by the user using the signal features included in the second biosignal. When the selected candidate path is accurately identified, the apparatus performs S430, and otherwise, the apparatus returns to S422 and waits for second biosignal measurement.

In more detail, first, when it is determined that collaboration between the moving body and the user is necessary to control the driving of the moving body based on a surrounding situation, surrounding information including at least one of a surrounding map, a surrounding image or a driving path of the moving body is provided to the user in the form of visual stimulation. In this instance, when the surrounding situation collected by the moving body satisfies a preset control change condition from the moving body to the user, it is desirable to visualize and display the surrounding information to allow the user to visually distinguish the plurality of candidate paths on which the moving body may drive. Since the surrounding information collected by the moving body to control the autonomous driving itself is in the form of an electrical signal or computer data, it is necessary to convert the surrounding information into a form that is easy for human to understand. Subsequently, a second biosignal evoked by recognition of the surrounding information from the user is acquired, and one of the plurality of candidate paths included in the surrounding information is identified. In this instance, the user's intended candidate path may be identified by acquiring the second biosignal from the user having recognized the visual stimulation related to the surrounding information. Subsequently, a detailed driving direction of the moving body may be determined based on the identified candidate path, and after a spontaneous biosignal elicited by MI is extracted from the second biosignal, the detailed driving direction of the moving body intended by the user may be determined based on the identified candidate path.

Figure 7:
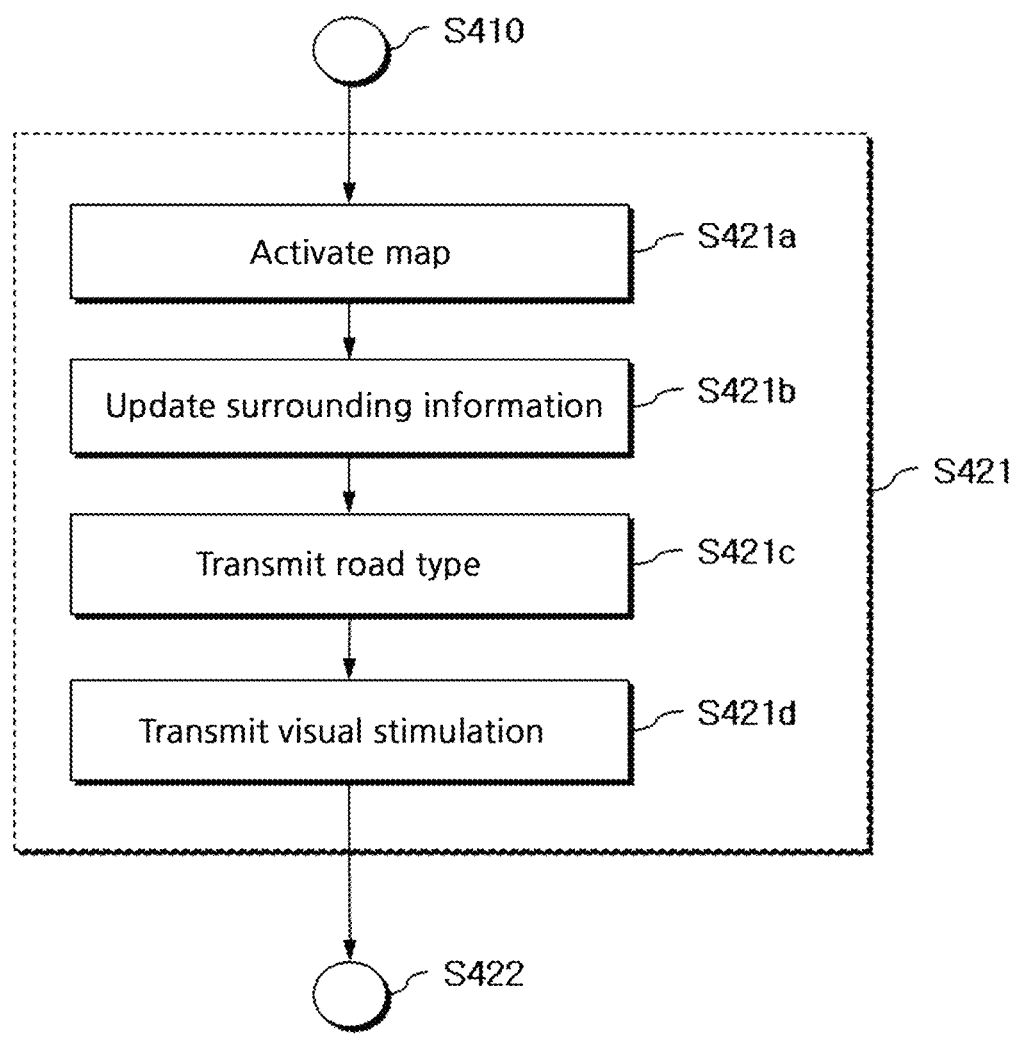
FIGS. 7 and 8 are diagrams showing an exemplary implementation process of providing surrounding information of a remote area and processing stimulation in the visual stimulation activation process of FIG. 6.
Figure 8:
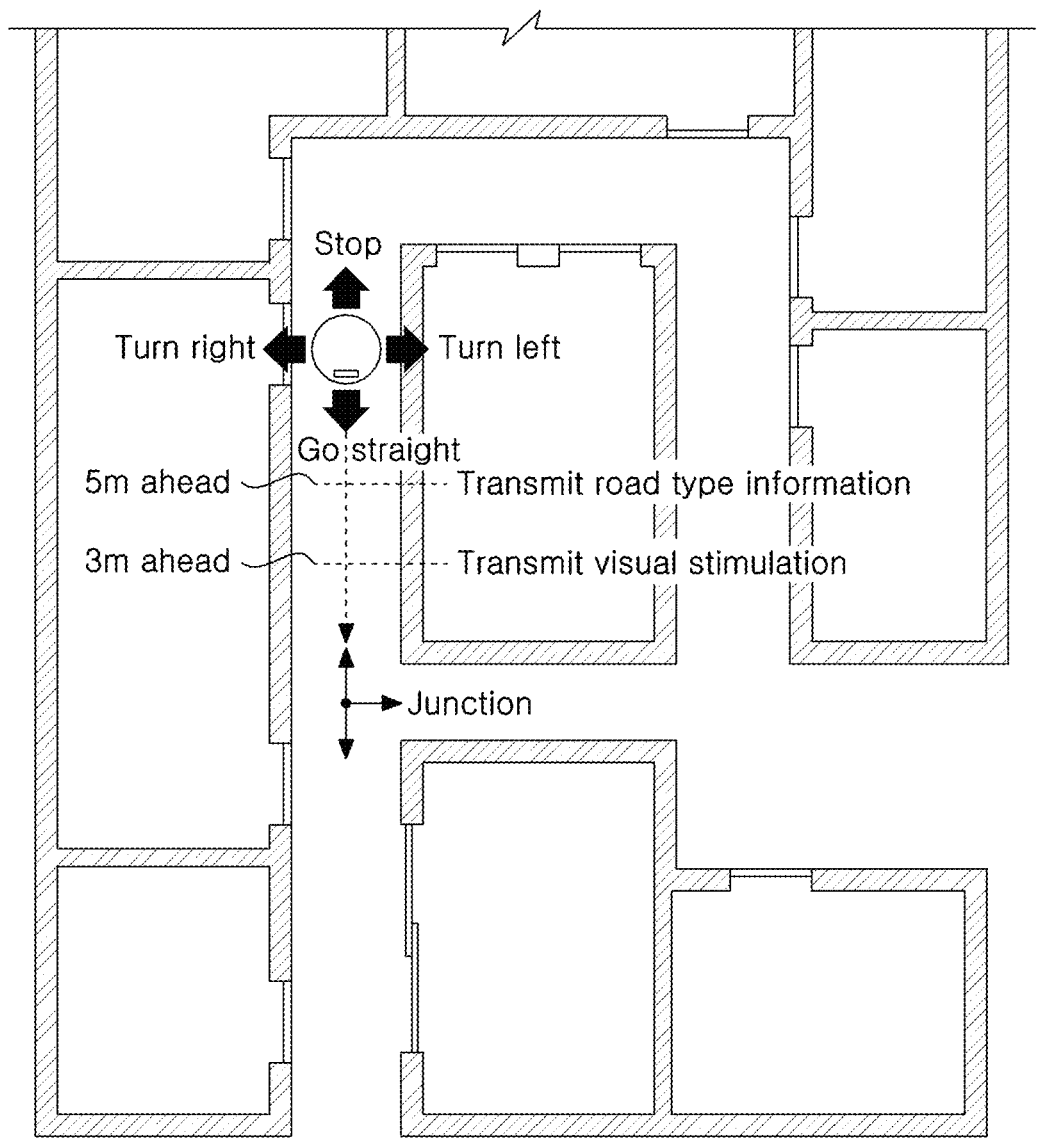

FIGS. 7 and 8 are diagrams illustrating an exemplary implementation process (S421) of providing surrounding information of the remote area and processing stimulation in the visual stimulation activation process of FIG. 6.

In S421*a*, a map for understanding and setting a driving path is activated, and in S421*b*, surrounding information of the moving body is updated. From the perspective of implementation, a junction near the current driving path of the moving body may be identified by receiving the surrounding information including at least one of a surrounding map, a surrounding image or a driving path of the moving body.

In S421*c*, the type of road ahead is transmitted to the user. That is, type information associated with the driving path at a first estimated time at which the moving body approaches the identified junction is preferably provided to the user in the form of visual stimulation. Subsequently, in S421*d*, visual stimulation is acquired from the user and transmitted to the system. That is, a driving direction of the moving body may be determined by acquiring a second biosignal from the user having recognized the visual stimulation at a second estimated time at which the moving body approaches the identified junction. Here, the first estimated time refers to a point in time when the moving body arrives at a location farther away from the target (the junction) than the second estimated time, and will be a longer distance in the geometric sense. The first estimated time and the second estimated time may be adjusted, taking the remaining distance to the junction and the speed of the moving body into account.

Referring to FIG. 8, the drawing shows that information associated with the road ahead is set with varying conditions for each of the two estimated times, and these settings correspond to the control change condition introduced previously. That is, the moving body that controls the driving itself determines the surrounding situation, and when it is determined that collaboration between the moving body and the user is necessary to control the driving of the moving body (when the control change condition is satisfied), the user's control is intervened through provision of additional information from the moving body to the user.

First, the point in time at which the moving body arrives 5 m ahead of the junction will be the first estimated time, and the point in time at which the moving body arrives 3 m ahead of the junction will be the second estimated time. For example, information associated with the type of road is provided to the user at the first estimated time, and visual stimulation (the second biosignal) for BCI-based direction setting is detected at the second estimated time, thereby achieving smooth driving of the moving body without a time delay caused by signal processing, which is the disadvantage of the general BCI-based control system. That is, it is possible to induce the user to recognize and quickly select the path before reaching the target (the junction) through collaboration between the moving body and the user, thereby allowing the moving body to operate according to the predetermined selection at the point in time when the moving body reaches the target.

Figure 9:
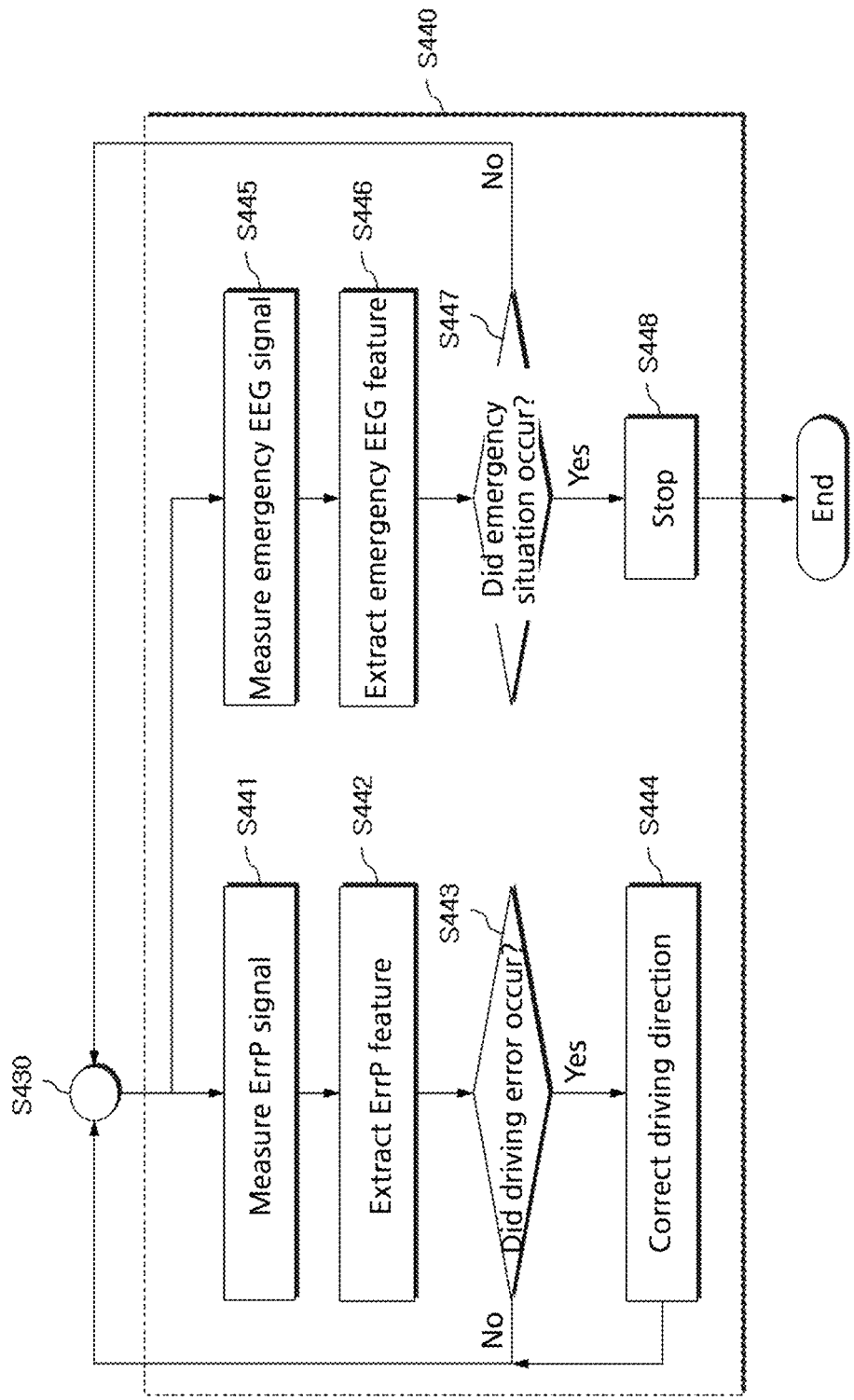
FIG. 9 is a detailed flowchart showing a process of processing an error or an emergency situation in the method for controlling a moving body of FIG. 4 according to an embodiment of the present disclosure.

FIG. 9 is a detailed flowchart showing the process of processing an error or an emergency situation in the method for controlling a moving body of FIG. 4 according to an embodiment of the present disclosure.

When a biosignal (for example, an ErrP pattern) indicating error recognition is inputted in S441, ErrP features may be extracted in S442, and an occurrence of a driving error may be detected in S443. When an occurrence of a driving error is detected, the driving direction is corrected in S444. In this process, the remote moving body may start rotating at its position, detect a biosignal indicating an intention to start the operation in a direction in the user wants to drive, and correct the driving path into the direction. Through this method, the direction may be also corrected to a free angle, and if necessary, a backward direction is possible. In summary, the apparatus for controlling a moving body may acquire a third biosignal (for example, ErrP) responsive to recognition of the driving error from the user and correct the driving direction of the moving body to induce the resetting of the driving path.

In S445, an EEG signal responsive to recognition of an emergency situation may be measured from the user, in S446, features of the corresponding signal may be extracted, and in S447, an occurrence of an emergency situation may be detected. When an occurrence of an emergency situation is detected, the system may be immediately stopped in S448.

Figure 10:
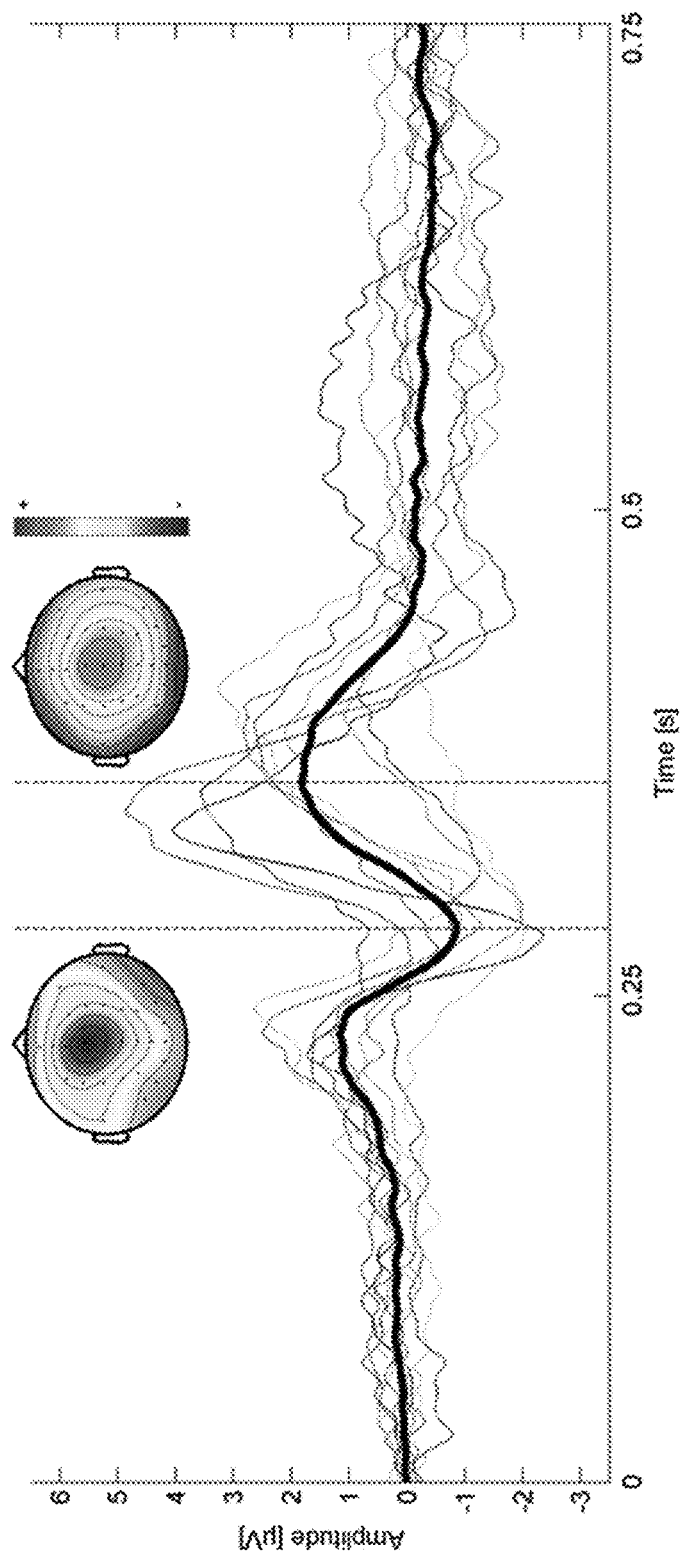
FIG. 10 is a diagram illustrating EEG that may be used to detect a user's error recognition.

FIG. 10 is a diagram illustrating EEG that may be used to detect the user's error recognition, and a biosignal for detecting error recognition is preferably an error-related potential (ErrP) signal acquired through the EEG measuring means.

Figure 11:
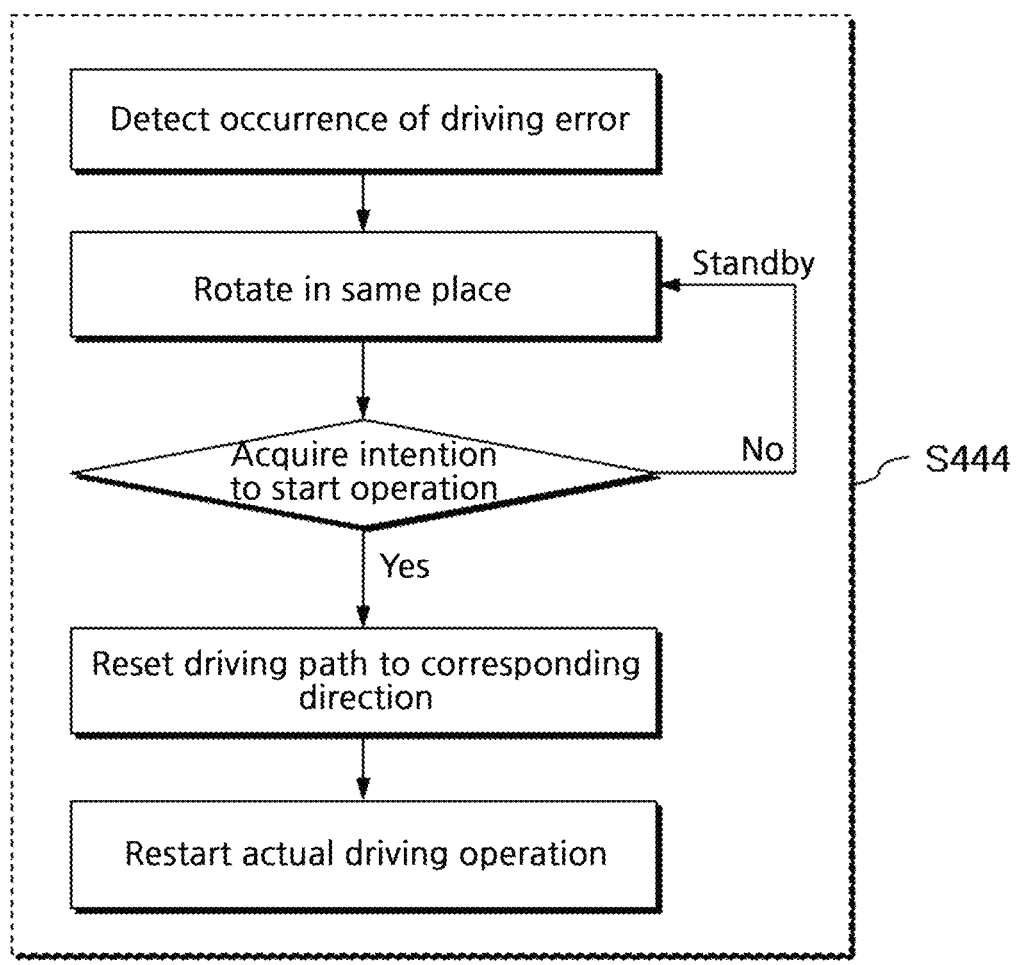
FIG. 11 is a detailed flowchart showing a process of correcting a driving direction in the error processing process of FIG. 9 according to an embodiment of the present disclosure.

FIG. 11 is a detailed flowchart showing the process (S444) of correcting the driving direction in the error processing process of FIG. 9 according to an embodiment of the present disclosure.

First, when the apparatus for controlling a moving body acquires a third biosignal (for example, ErrP) responsive to recognition of a driving error from the user, the apparatus for controlling a moving body determines that a driving error occurred, and controls the moving body not to drive along the incorrect path. To this end, the moving body may start rotating at its position itself (or change its direction for a correct path, or if necessary, move back). While the moving body is rotating, a biosignal indicating an intention to start the operation in the user's desired driving direction may be acquired. That is, a direction at the point in time when the biosignal indicating an intention to start the operation is acquired corresponds to a correct driving direction initially intended by the user. Accordingly, it is desirable that the apparatus for controlling a moving body resets the driving path to the corresponding direction. Subsequently, the apparatus for controlling a moving body may command the moving body to perform an actual driving operation along the reset driving path. In summary, the apparatus for controlling a moving body may acquire a third biosignal (for example, ErrP) responsive to recognition of a driving error from the user and correct the driving direction of the moving body to induce the resetting of the driving path.

Figure 12:
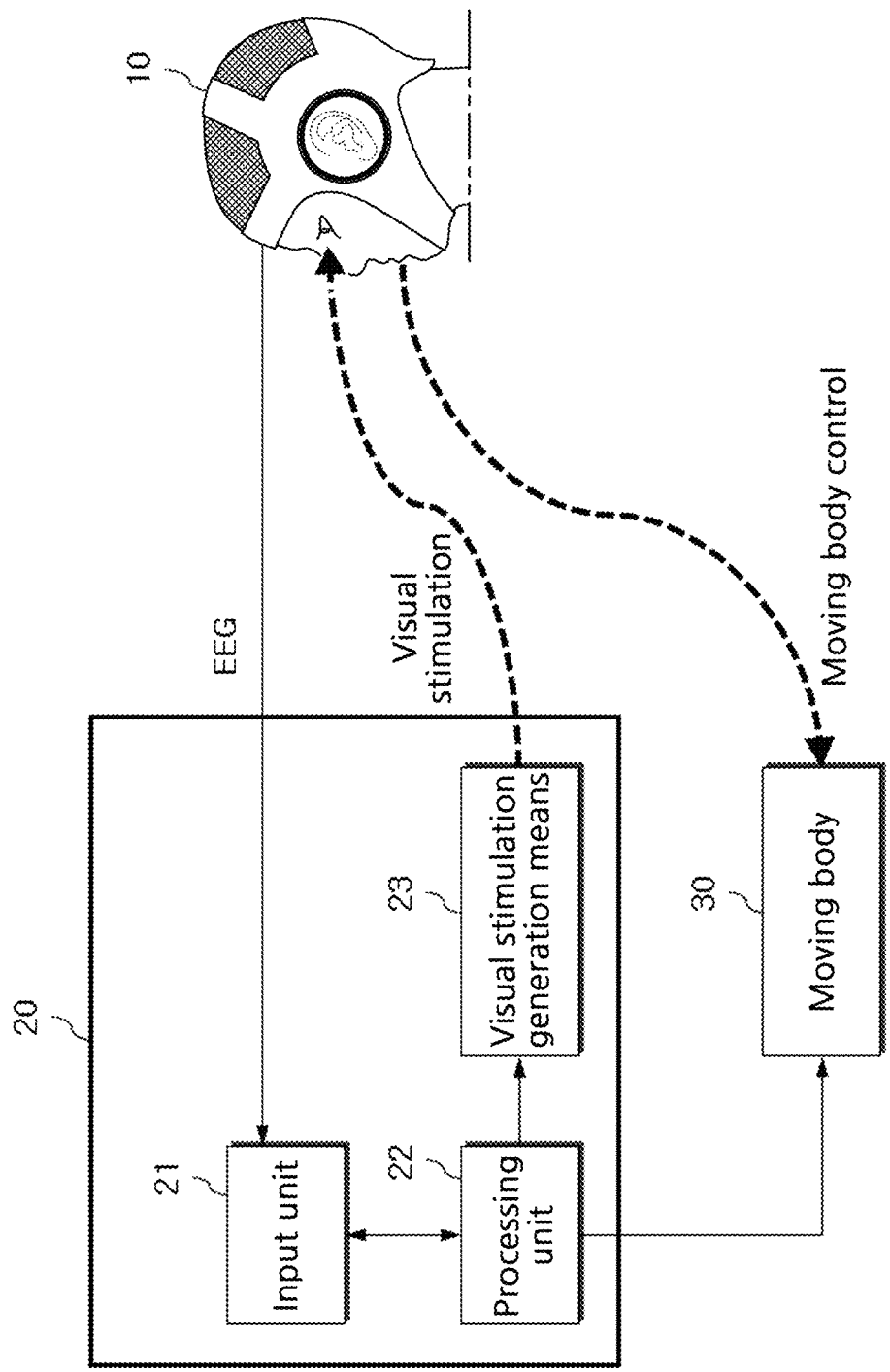
FIG. 12 is a block diagram showing an apparatus for controlling a moving body based on BCI according to another embodiment of the present disclosure.

FIG. 12 is a block diagram showing an apparatus for controlling a moving body based on BCI according to another embodiment of the present disclosure, and is a re-configuration of the method for controlling a moving body described through FIG. 4 from the perspective of hardware configuration of the remote moving body. Accordingly, to avoid redundancy, the operation and function of each element of the apparatus will be briefly described on the premise of an assistive eating situation.

The apparatus 20 for controlling a moving body includes an input unit 21 to receive inputs of a plurality of types of biosignals measured from a user 10, a processing unit 22 to generate a control signal for controlling a moving body 30 according to the type of biosignal, and a visual stimulation generation means 23 to visualize and display surrounding information to allow the user 10 to visually distinguish the plurality of candidate paths on which the moving body 30 may drive. For convenience of description, although the drawing shows that the apparatus 20 for controlling a moving body and the moving body 30 are separated, the two may be provided in one physical device. That is, the apparatus 20 for controlling a moving body is attached to the body of the moving body 30 that controls the autonomous driving for collaborative control with the user.

The processing unit 22 acquires a first biosignal indicating an intention to start the operation of the moving body 30 from the user 10, operates the moving body 30, determines a surrounding situation of the moving body 30 that controls the driving itself, when the surrounding situation collected by the moving body satisfies a preset control change condition from the moving body 30 to the user 10, provides the user 10 with surrounding information of the moving body for inducing the path setting through the visual stimulation generation means, acquires a second biosignal evoked by recognition of the surrounding information from the user 10, sets a driving direction of the moving body 30, commands the moving body 30 to automatically perform a driving operation to be carried out in the set driving direction, acquires a third biosignal responsive to recognition of a driving error from the user 10, and corrects the driving direction of the moving body 30 to induce the resetting of the driving path. In this instance, the first biosignal, the second biosignal and the third biosignal are preferably different types of EEG signals acquired through one EEG measuring means attached to the user 10.

When it is determined that collaboration between the moving body 30 and the user 10 is necessary to control the driving of the moving body based on the surrounding situation, the processing unit 22 may provide the user 10 with surrounding information including at least one of a surrounding map, a surrounding image or a driving path of the moving body 30 in the form of visual stimulation, acquire a second biosignal evoked by recognition of the surrounding information from the user 10, identify one of a plurality of candidate paths included in the surrounding information, and determine a detailed driving direction of the moving body 30 based on the identified candidate path. In this instance, the processing unit 22 may acquire the second biosignal from the user 10 having recognized the visual stimulation associated with the surrounding information, identify the user's intended candidate path, extract a spontaneous biosignal elicited by MI from the second biosignal, and determine the detailed driving direction of the moving body intended by the user based on the identified candidate path.

Additionally, the processing unit 22 receives surrounding information including at least one of a surrounding map, a surrounding image or a driving path of the moving body 30, identifies a junction near the current driving path of the moving body, provides the user 10 with type information associated with a driving path at a first estimated time at which the moving body approaches the identified junction in the form of visual stimulation, acquires a second biosignal from the user 10 having recognized the visual stimulation at a second estimated time at which the moving body approaches the identified junction, and determines a driving direction of the moving body, and the first estimated time and the second estimated time may be adjusted, taking the remaining distance to the junction and the speed of the moving body into account.

Further, the processing unit 22 may acquire a third biosignal responsive to recognition of a driving error from the user 10, investigate if the set driving direction mismatches the intention of the user 10, and as a result of the investigation, when there is an error in the set driving direction, command the moving body 30 to rotate at its place to correct the driving direction, and when a biosignal indicating an intention to start the operation in a driving direction desired by the user 10 is acquired while the moving body 30 is rotating, command the moving body 30 to perform an actual driving operation along the driving path reset to the corresponding direction.

Figure 13:
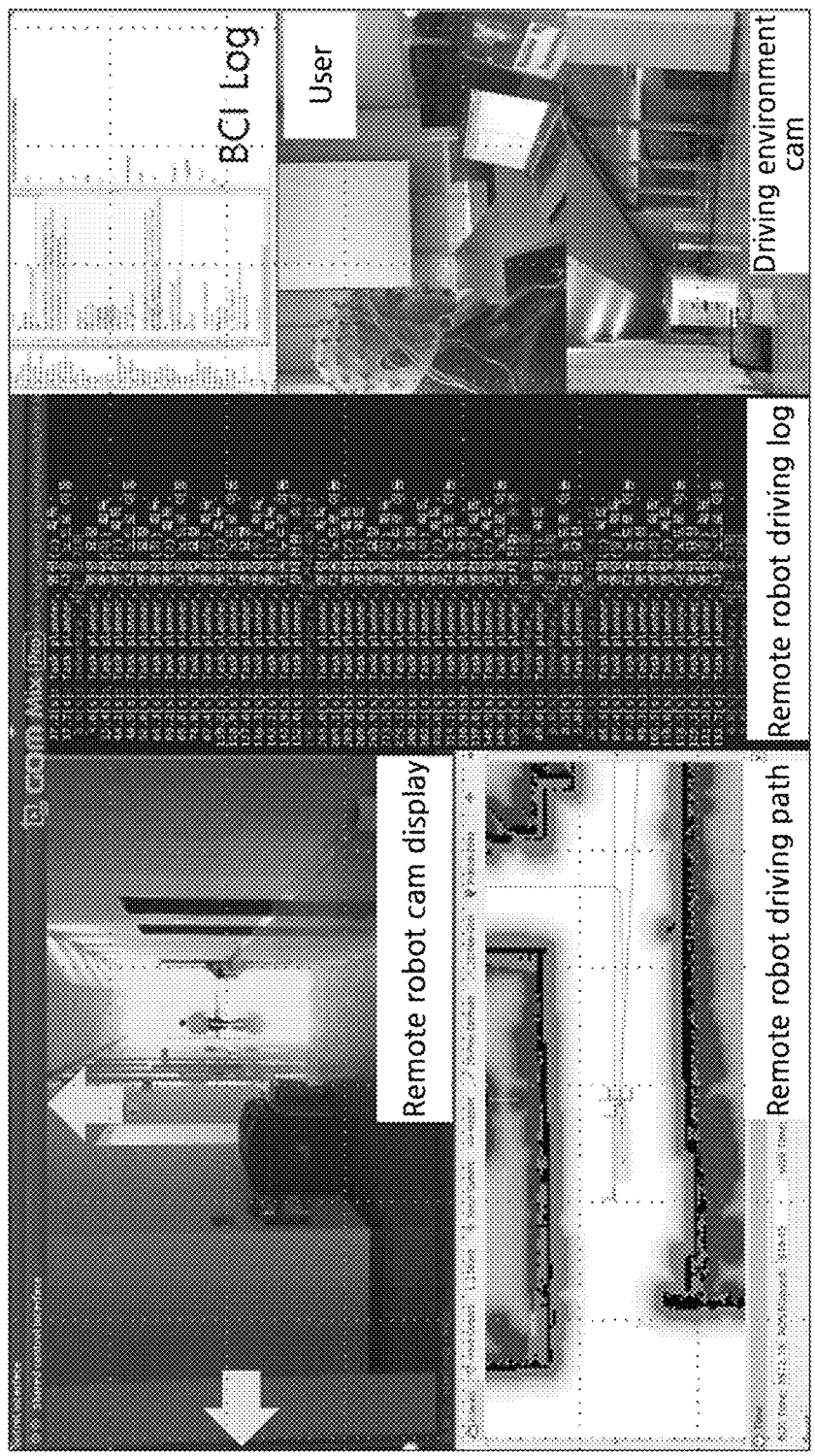
FIG. 13 shows a system implementation example in which a remote robot determines remote area driving information and situations and transmits information associated with a driving path, and is controlled using BCI according to still another embodiment of the present disclosure.

FIG. 13 shows a system implementation example in which the remote control robot determines remote area driving information and situations and transmits information associated with a driving path, and is controlled using BCI according to still another embodiment of the present disclosure.

Referring to FIG. 13, the exemplary moving body control system performs signal processing based on EEG and classification of the user's intention, presents surrounding information of the remote area, and controls the driving of the remote moving body using the BCI system. Through the corresponding system, it is possible to allow the user to drive the remote moving body beyond the traditional simple transmission technology of images of the remote area, and through this, assist various social activities.

According to the above-described embodiments of the present disclosure, it is possible to identify each of various EEGs of the user, such as an EEG indicating the operation of the BCI system, an EEG evoked by visual stimulation, an EEG evoked by MI and an EEG evoked by error response and efficiently control the moving body according to information associated with a driving path provided by the smart moving body, thereby improving the processing rate which is the disadvantage of BCI, and accurately set a detailed driving path of the user's desired target object by sequential BCI control and control the moving body to drive according to the user's desired destination, thereby inducing the user with physical impairment to do active and independent activities according to the user's intention and enhancing the self-esteem as well as reducing the labor, time and cost required to help the user.

Further, the embodiments of the present disclosure can be used to control the exemplary moving body (a driving robot) as well as devices used in daily life or physical assistant robots, and have commercial applications in smart home, healthcare, silver industry and game industry.

Meanwhile, the embodiments of the present disclosure may be implemented in computer-readable code on computer-readable recording media. The computer-readable recording media include all types of recording devices for storing data that can be read by a computer system.

Examples of the computer-readable recording media include read-only memory (ROM), random access memory (RAM), compact disc read-only memory (CD-ROM), magnetic tape, floppy disk and optical data storage devices. Additionally, the computer-readable recording media may be distributed over computer systems connected via a network to store and execute the computer-readable code in a distributed manner. Additionally, functional programs, code and code segments for implementing the present disclosure may be easily inferred by programmers in the technical field pertaining to the present disclosure.

The present disclosure has been hereinabove described based on various embodiments. Those having ordinary skill in the technical field pertaining to the present disclosure will understand that the present disclosure may be embodied in modified forms without departing from the essential features of the present disclosure. Therefore, the embodiments disclosed herein should be considered in a descriptive sense, not in a limiting sense. The scope of the present disclosure is defined in the appended claims, not in the above-described description, and it should be interpreted that the present disclosure covers all differences within its equivalent scope.

DETAILED DESCRIPTION OF MAIN ELEMENTS

10: User (or Biosignal/EEG measuring means attached to the user)
20: Apparatus for controlling a moving body
21: Input unit
22: Processing unit
23: Visual stimulation generation means
30: Moving body (Driving robot)

What is claimed is:

1. A method for controlling a moving body, comprising:
    acquiring, by an apparatus for controlling a moving body, a first biosignal indicating an intention to start operation of the moving body from a user, and operating the moving body;
    determining, by the apparatus for controlling a moving body, a surrounding situation of the moving body that autonomously controls driving of the moving body, providing the user with surrounding information about the surrounding situation of the moving body for inducing path setting, acquiring a second biosignal evoked by recognition of the surrounding information from the user, and setting a driving direction of the moving body;
    commanding, by the apparatus for controlling a moving body, the moving body to automatically perform a driving operation to be carried out in the set driving direction; and
    acquiring, by the apparatus for controlling a moving body, a third biosignal responsive to recognition of a driving error from the user and correcting the set driving direction of the moving body to induce driving path resetting.

2. The method for controlling a moving body according to claim 1, wherein the first biosignal, the second biosignal and the third biosignal are different types of electroencephalogram (EEG) signals acquired through one EEG measuring means.

3. The method for controlling a moving body according to claim 1, wherein the acquiring the first biosignal comprises:
    receiving inputs of biosignals from the user having recognized the moving body, and acquiring the first biosignal indicating the intention to start the operation of the moving body among the inputted biosignals; and
    operating the moving body in response to the first biosignal and waiting for a driving direction selection of the user.

4. The method for controlling a moving body according to claim 1, wherein the determining the surrounding situation comprises:
    when it is determined that collaboration between the moving body and the user is necessary to control the driving of the moving body based on the surrounding situation, providing the user with the surrounding information, the surrounding information including at least one of a surrounding map, a surrounding image or a driving path of the moving body in a form of visual stimulation;
    acquiring the second biosignal evoked by recognition of the surrounding information from the user, and identifying one of a plurality of candidate paths included in the surrounding information; and
    determining a detailed driving direction of the moving body based on the identified candidate path.

5. The method for controlling a moving body according to claim 4, wherein the providing the user with the surrounding information comprises visualizing and displaying the surrounding information to allow the user to visually distinguish the plurality of candidate paths on which the moving body may drive, when the surrounding situation collected by the moving body satisfies a preset control change condition for changing control from the moving body to the user.

6. The method for controlling a moving body according to claim 4, wherein the identifying one of the plurality of candidate paths includes identifying an intended candidate path of the user.

7. The method for controlling a moving body according to claim 4, wherein the determining the detailed driving direction comprises extracting a spontaneous biosignal elicited by motor imagery from the second biosignal, and determining that the detailed driving direction of the moving body is intended by the user based on the identified candidate path.

8. The method for controlling a moving body according to claim 1, wherein the determining the surrounding situation comprises:
    receiving the surrounding information, the surrounding information including at least one of a surrounding map, a surrounding image or a driving path of the moving body, and identifying a junction near a current driving path of the moving body;
    providing the user with type information associated with a driving path at a first estimated time at which the moving body approaches the identified junction in a form of visual stimulation; and
    acquiring the second biosignal from the user, the user having recognized the visual stimulation at a second estimated time at which the moving body approaches the identified junction, and determining the set driving direction of the moving body.

9. The method for controlling a moving body according to claim 8, wherein the first estimated time and the second estimated time are adjusted, taking a remaining distance to the junction and a speed of the moving body into account.

10. The method for controlling a moving body according to claim 1, wherein the acquiring the third biosignal comprises:
    acquiring the third biosignal responsive to recognition of a driving error from the user, and investigating if the set driving direction mismatches the user's intention;

as a result of the investigation, when there is an error in the set driving direction, commanding the moving body to rotate at a same position to correct the driving direction; and when a biosignal indicating an intention to start operation is acquired in a desired driving direction of the user while the moving body is rotating, commanding the moving body to perform an actual driving operation along the driving path, the driving path being reset to a corresponding direction.

11. The method for controlling a moving body according to claim 1, wherein the first biosignal is at least one of an EEG double blink signal acquired through an EEG measuring means, an audio signal acquired through a microphone, or a motion or gesture signal acquired through a camera, the second biosignal is a steady-state visual evoked potential (SSVEP) signal or a motor imagery (MI) signal acquired through the EEG measuring means, and includes an EEG signal evoked by a visual recognition by the user of a plurality of candidate paths included in the surrounding information or MI, and the third biosignal is an error-related potential (ErrP) signal acquired through the EEG measuring means.

12. The method for controlling a moving body according to claim 1, wherein the acquiring the first biosignal does not move to the determining the surrounding situation, the commanding the moving body and the acquiring the third biosignal and is on standby until the first biosignal is acquired among a plurality of types of biosignals inputted from the user, the determining the surrounding situation does not move to the commanding the moving body and is on standby until the second biosignal is acquired among the plurality of types of biosignals inputted from the user, and after the commanding the moving body is completed, the acquiring the first biosignal or the determining the surrounding situation is performed to repeat the setting of the driving direction and the operation.

13. The method for controlling a moving body according to claim 1, further comprising:

acquiring, by the apparatus for controlling a moving body, a fourth biosignal responsive to recognition of an emergency situation from the user, and commanding the moving body to stop.

14. A non-transitory computer-readable recording medium having recorded thereon a program for enabling a computer to perform the method according claim 1.

15. An apparatus for controlling a moving body, comprising:

an input unit to receives inputs of a plurality of types of biosignals measured from a user;

a processing unit to generate a control signal for controlling the moving body according to a type of the biosignal; and a visual stimulation generation means to visualize and display surrounding information to allow the user to visually distinguish a plurality of candidate paths on which the moving body may drive, the plurality of candidate paths being included in the surrounding information, wherein the processing unit acquires a first biosignal indicating an intention to start operation of the moving body from the user, operates the moving body, determines a surrounding situation of the moving body that autonomously controls the driving, when the surrounding situation determined by the processing unit satisfies a preset control change condition for changing control from the moving body to the user, provides the user with surrounding information of the moving body for inducing path setting through the visual stimulation generation means, acquires a second biosignal evoked by recognition of the surrounding information from the user, sets a driving direction of the moving body, commands the moving body to automatically perform a driving operation to be carried out in the set driving direction, acquires a third biosignal responsive to recognition of a driving error from the user, and corrects the driving direction of the moving body to induce driving path resetting.

16. The apparatus for controlling a moving body according to claim 15, wherein when it is determined that collaboration between the moving body and the user is necessary to control driving of the moving body based on the surrounding situation, the processing unit provides the user with the surrounding information, the surrounding information including at least one of a surrounding map, a surrounding image or a driving path of the moving body in a form of visual stimulation, acquires the second biosignal evoked by recognition of the surrounding information from the user, identifies one of the plurality of candidate paths included in the surrounding information, and determines a detailed driving direction of the moving body based on the identified candidate path.

17. The apparatus for controlling a moving body according to claim 16, wherein the processing unit acquires the second biosignal from the user having recognized the visual stimulation of the surrounding information, identifies an intended candidate path of the user, extracts a spontaneous biosignal elicited by motor imagery (MI) from the second biosignal, and determines the detailed driving direction of the moving body intended by the user based on the identified candidate path.

18. The apparatus for controlling a moving body according to claim 15, wherein the processing unit receives the surrounding information, the surrounding information including at least one of a surrounding map, a surrounding image or a driving path of the moving body, identifies a junction near a current driving path of the moving body, provides the user with type information associated with a driving path at a first estimated time at which the moving body approaches the identified junction in a form of visual stimulation, acquires the second biosignal from the user having recognized the visual stimulation at a second estimated time at which the moving body approaches the identified junction, and determines the driving direction of the moving body, and the first estimated time and the second estimated time are adjusted, taking a remaining distance to the junction and a speed of the moving body into account.

19. The apparatus for controlling a moving body according to claim 15, wherein the processing unit acquires the third biosignal responsive to recognition of a driving error from the user, investigates if the set driving direction mismatches the user's intention, as a result of the investigation, when there is an error in the set driving direction, commands the moving body to rotate at a same position to correct the driving direction, and when a biosignal indicating an intention to start operation is acquired in a desired driving direction of the user while the moving body is rotating, commands the moving body to perform an actual driving operation along the driving path, the driving path being reset to a corresponding direction.

20. The apparatus for controlling a moving body according to claim 15, wherein the first biosignal is at least one of an EEG double blink signal acquired through an EEG measuring means, an audio signal acquired through a microphone, or a motion or gesture signal acquired through a camera,
  the second biosignal is a steady-state visual evoked potential (SSVEP) signal or a motor imagery (MI) signal acquired through the EEG measuring means, and includes an EEG signal evoked by a visual recognition by the user of the plurality of candidate paths included in the surrounding information or MI, and
  the third biosignal is an error-related potential (ErrP) signal acquired through the EEG measuring means.

* * * * *